(12) United States Patent
Kuehnle et al.

(10) Patent No.: US 7,145,041 B2
(45) Date of Patent: *Dec. 5, 2006

(54) METHOD FOR PRODUCING SATURATED ALCOHOLS, KETONES, ALDEHYDES AND CARBOXYLIC ACIDS

(75) Inventors: Adolf Kuehnle, Marl (DE); Carsten Jost, Marl (DE); Roger Arthur Sheldon, VA Rijswijk (NL); Sandrine M. M. Chatel, ZV Pijnacker (NL); Isabella W. C. E. Arends, SL's Gravenhage (NL)

(73) Assignee: Degussa AG, Dusseldorf (DE)

( * ) Notice: Subject to any disclaimer, the term of this patent is extended or adjusted under 35 U.S.C. 154(b) by 121 days.

This patent is subject to a terminal disclaimer.

(21) Appl. No.: 10/482,777

(22) PCT Filed: Jun. 12, 2002

(86) PCT No.: PCT/EP02/06411

§ 371 (c)(1),
(2), (4) Date: Jun. 25, 2004

(87) PCT Pub. No.: WO03/004447

PCT Pub. Date: Jan. 16, 2003

(65) Prior Publication Data

US 2004/0249197 A1    Dec. 9, 2004

(30) Foreign Application Priority Data

Jul. 2, 2001    (DE) .............................. 101 31 522

(51) Int. Cl.
C07C 45/00 (2006.01)
C07C 35/00 (2006.01)
C07C 27/00 (2006.01)
C07C 51/10 (2006.01)

(52) U.S. Cl. .............. 568/344; 568/346; 568/351; 568/389; 568/830; 568/836; 562/497; 562/512.2

(58) Field of Classification Search ............ 568/344, 568/346, 351, 389, 830, 836; 562/497, 512.2
See application file for complete search history.

(56) References Cited

U.S. PATENT DOCUMENTS 4,940,819 A * 7/1990 Kiel et al. ............ 568/318

| 5,030,739 | A | 7/1991 | Foricher et al. | 552/542 |
|---|---|---|---|---|
| 5,958,821 | A * | 9/1999 | Ishii et al. | 502/167 |
| 6,166,268 | A | 12/2000 | Kuehnle et al. | 568/800 |
| 6,210,557 | B1 | 4/2001 | Stochniol et al. | 205/413 |
| 6,852,893 | B1 * | 2/2005 | Kuhnle et al. | 568/314 |

FOREIGN PATENT DOCUMENTS

EP    858835    8/1998

OTHER PUBLICATIONS

Y. Ishii: "A novel catalysis of N-hydroxyphthalimide in the oxidation of organic substrates by molecular oxygen" Journal of Organic Chemistry, vol. 60, No. 13, 1995, pp. 3934-3934.
A. Horinaka:"Photosensitized oxygenation of unconjugated cyclic dienes" Bulletin of the Chemical Society of Japan, vol. 48, No. 7, 1975, pp. 2095-2098.
U.S. Appl. No. 10/239,185, filed Sep. 26, 2002, Kuehnle et al.
U.S. Appl. No. 10/239,215, filed Jan. 15, 2003, Kuehnle et al.
U.S. Appl. No. 10/482,777, filed Jan. 2, 2004, Kuehnle et al.
U.S. Appl. No. 07/261,145, filed Oct. 24, 1988, Kuenhnle et al.
U.S. Appl. No. 09/866,636, filed May 30, 2001, Kuehnle et al.
U.S. Appl. No. 09/866,638, filed May 30, 2001, Van Berkel et al.
U.S. Appl. No. 09/842,808, filed Apr. 27, 2001, Lenke et al.
U.A. Appl. No. 07/577,099, filed Sep. 4, 1990, Kuehnle et al.
U.S. Appl. No. 10/005,108, filed Dec. 7, 2002, Abbenhuis et al.
U.S. Appl. No. 10/005,107, filed Dec. 7, 2001, Jost et al.
U.S. Appl. No. 10/210,082, filed Aug. 2, 2002, Jost et al.
U.S. Appl. No. 10/399,781, filed Oct. 23, 2003, Kuehnle et al.

* cited by examiner

Primary Examiner—Johann R. Richter
Assistant Examiner—Sikarl A. Witherspoon
(74) Attorney, Agent, or Firm—Oblon, Spivak, McClelland, Maier & Neustadt, P.C.

(57) ABSTRACT

The invention relates to a method for catalytically oxidizing unsaturated hydrocarbons to form oxidation products, and to the production of saturated alcohols, ketones, aldehydes or carboxylic acids by subsequently hydrogenating the oxidation product. A compound of formula (I) is used as a catalyst during oxidizing in which: R1, R2=H, an aliphatic or aromatic alkoxy radical, carboxyl radical, alkoxycarbonyl radical or hydrocarbon radical, each having 1 to 20 carbon atoms, SO3H, NH2, OH, F, Cl, Br, I and/or NO2, whereby R1 and R2 signify identical or different radicals or R1 and R2 can be coupled to one another via a covalent bond, with Q1, Q2=the same or different, C, CH, N; X, Z=C, S or CH2; Y=O or OH; k=0, 1 or 2; 1=0, 1 or 2; m=1 to 100 in the presence of a radical initiator. Peroxy compounds or azo compounds can be used as radical initiators. Preferred substrates are cyclic aliphatic or aromatic compounds.

20 Claims, No Drawings

METHOD FOR PRODUCING SATURATED ALCOHOLS, KETONES, ALDEHYDES AND CARBOXYLIC ACIDS

The invention relates to a process for preparing saturated alcohols, ketones, aldehydes and carboxylic acids by catalytic oxidation of unsaturated hydrocarbons and subsequent hydrogenation of the oxidation products.

The oxidation of hydrocarbons is an important reaction in industrial organic chemistry. For these oxidations, compounds such as $KMnO_4$, $CrO_3$ or $HNO_3$ can be used as oxidizing agents. However, firstly, these have the disadvantage of a relatively high price, and secondly their use is accompanied with unwanted by-products which can lead to disposal problems and ecological pollution.

Preferably, therefore, oxidizing agents based on peroxides or $N_2O$ are used. The cheapest oxidizing agent, however, is molecular oxygen, either in pure form or as atmospheric oxygen. Oxygen itself, however, is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds. A great number of industrial processes are based on the metal-catalyzed autoxidation of hydrocarbons. Thus, for example, the oxidation of cyclohexane with $O_2$ to cyclohexanol or cyclohexanone proceeds with the use of manganese or cobalt salts ("Industrielle Organische Chemie" [Industrial organic chemistry] 1994, 260, VCH Verlagsgesellschaft mbH Weinheim). These industrial processes are based on a free-radical chain mechanism. The biradical oxygen reacts with a hydrocarbon free radical, with formation a peroxy radical and subsequent chain propagation by abstraction of an H atom at a further hydrocarbon. In addition to metal salts, however, organic molecules can also act as free-radical initiators.

It is a disadvantage with these processes that the selectivity decreases very greatly with increasing conversion rate and therefore the processes must be operated at a very low level of conversion rate. Thus, for example, the oxidation of cyclohexane to cyclohexanol/cyclohexanone is carried out at a conversion rate of 10 to 12% so that the selectivity is 80 to 85% ("Industrielle Organische Chemie" [Industrial Organic Chemistry] 1994, 261, VCH Verlagsgesellschaft mbH, Weinheim). In a further important industrial autoxidation process, oxidation of cumene to cumene hydroperoxide, the conversion rate is about 30% for a cumene hydroperoxide selectivity of approximately 90% ("Industrielle Organische Chemie" [Industrial Organic Chemistry] 1994, 383, VCH Verlagsgesellschaft mbH Weinheim).

An alternative to metal catalysts is the use of catalyst systems, for example N-hydroxyphthalimide (NHPI). However, the reaction rate for the processes presented is not satisfactory, despite the high amount of catalyst (up to equimolar ratios versus the substrate) (J. Mol. Catalysis A. 1997, 117, 123–137). U.S. Pat. No. 5,030,739 describes the use of N-hydroxydicarboxylic acid imides for the allylic oxidation of isoprene derivatives to the corresponding acrolein compounds.

In general, amounts of catalyst of at least 10 mol % with respect to the substrate are used, with higher amounts of catalyst being used to increase the reaction rate (J. Org. Chem. 1995, 60, 3934–3935).

A further development of the system is the use of co-catalysts. Co-catalysts which can be used are metal compounds, in particular heavy metal salts, enzymes or strong Brönsted acids. Thus Ishii et al. found that NHPI, in combination with metal salts as co-catalyst, can have advantages compared with the oxidation with NHPI but without metal salt (for example EP 0878234, EP 0864555, EP 0878458, EP 0858835, JP 11180913, J. Mol. Catalysis A. 1997, 117, 123–137). However, disadvantages of these systems are, in addition to the unwanted heavy metal content, also in this case the high amount of NHPI used. In order to ensure a satisfactory reaction rate, at least 10 mol % of catalyst must be used. A further disadvantage is that the redox metals used in part catalyze further reactions of the products and thus decrease the selectivity of the reaction.

Processes have also become known which use only a catalyst without co-catalyst. However, these are limited to oxidizing particularly activated substrates, such as ethers, esters or isoprene derivatives.

A further process variant is the use of NHPI together with alcohols or aldehydes (Chem. Commun. 1999, 727 728, Tetrahedron Letters 1999, 40, 2165–2168, Chem. Commun. 1997, 447–448). Disadvantages of these processes are the formation of coupling products and the high catalyst/substrate ratio used (10 mol %).

DE 19723890 describes an oxidation system consisting of an organic catalyst (3-amino-NHPI) and the redox enzyme laccase for preparing aromatic and heteroaromatic aldehydes and ketones. Here also, the amount of catalyst used is very high. In addition, this process, due to the use of an enzyme, has a complicated reaction system using a biologically necessary buffer system, which restricts the broad applicability of this system. Use of NHPI to oxidize olefins, in combination with subsequent hydrogenation, has not yet been described.

It was an object of the present invention to convert unsaturated hydrocarbons, selectively by oxidation, into saturated alcohols, aldehydes or ketones. For this, in particular, no heavy metal salts, for example cobalt acetate, should be used.

Surprisingly it has been found that compounds of the type

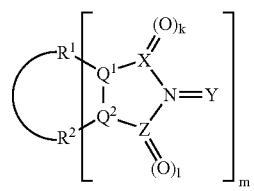

I can be used for the allylic oxidation of unsaturated hydrocarbons and that a subsequent hydrogenation of the oxidation product is sufficient to reduce the number of isomers formed in the oxidation and thus saturated oxygen-functionalized products can be prepared with high selectivity.

The present invention therefore relates to a process for preparing saturated alcohols, ketones, aldehydes, ketones and carboxylic acids, the starting compound used being an unsaturated hydrocarbon which is oxidized with an oxygen-containing gas, using a catalyst and in the presence of a free-radical initiator to form an oxidation product, and the catalyst used being a compound of the formula I

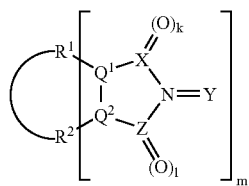

where $R^1$, $R^2$=H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$, where $R^1$ and $R^2$ are identical or different radicals, or $R^1$ and $R^2$ can be linked to one another via a covalent bond, $Q_1$, $Q_2$=C, CH or N, identical or different, X, z=C, S or $CH_2$, Y=0 or OH, k=0, 1 or 2, l=0, 1 or 2 and m=1 to 100, which comprises the oxidation products being reduced by a subsequent hydrogenation and saturated alcohols, ketones, aldehydes and/or carboxylic acids being formed.

The inventive process has the advantage that unsaturated hydrocarbons can be converted to alcohols, aldehydes and ketones by means of oxidation even without co-catalyst, heavy metals or strong acids. A further advantage of the combination of oxidation with the abovementioned catalyst and subsequent hydrogenation of the oxidation product is that the number of isomers formed in the oxidation is reduced and thus saturated, oxygen-functionalized products can be obtained with high selectivity. This is possible for the first time by the inventive combination of oxidation and hydrogenation. In oxidations of the prior art, without subsequent hydrogenation, a mixture of isomers is obtained, which can only be purified laboriously.

The inventive method for preparing saturated alcohols, ketones, aldehydes, ketones and carboxylic acids is distinguished in that the starting compound used is an unsaturated hydrocarbon which is first oxidized with an oxygen-containing gas using a catalyst and in the presence of a free-radical initiator, and the catalyst used is a compound of the formula I

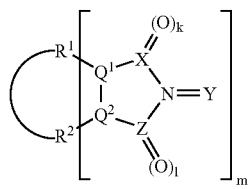

where $R^1$, $R^2$=H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$, where $R^1$ and $R^2$ are identical or different radicals, or $R^1$ and $R^2$ can be linked to one another via a covalent bond, $Q_1$, $Q_2$=C, CH or N, identical or different, X, Z=C, S or $CH_2$, Y=0 or OH, k=0, 1 or 2, l=0, 1 or 2 and m=1 to 100, and the oxidation products are reduced by a subsequent hydrogenation, as a result of which saturated alcohols, ketones, aldehydes and/or carboxylic acids are formed.

Examples of compounds of the formula I are N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxypyromellitimide, N,N'-dihydroxybenzophenone-3,3',4,4'tetracarboximide, N-hydroxymaleimide, N-hydoxypyridine-2,3-dicarboximide, N-hydroxysuccinimide, N-hydroxytartarimide, N-hydroxy-5-norbonene-2,3-dicarboximide, exo-N-hydroxy-7-oxabicyclo[2.2.1]hept-5-ene-2, 3-dicarboximide, N-hydroxy-cis-cyclohexane-1,2-dicarboximide, N-hydroxy-cis-4-cyclohexene-1,2-dicarboximide, N-hydroxynaphthalimide sodium salt, or N-hydroxy-obenzenedisulfonimides, hydantoin, and hydantoin derivatives and also N-hydroxysaccharin.

In the inventive process, no metal compounds or enzymes are used as co-catalyst. The process can be carried out in the absence of solvent, but preferably the process is carried out in organic solvents in the absence of strong acids; it is likewise possible to use an aqueous solution, the pH of which can vary in the weakly acidic to the basic range.

The oxidation is preferably carried out in such a manner that the molar ratio of catalyst to the hydrocarbon to be oxidized, that is to say the saturated and/or unsaturated cyclohydrocarbons, is from $10^{-8}$ to 1, preferably from $10^{-7}$ to 0.5, very particularly preferably from $10^{-6}$ to 0.2, and in a special embodiment is from $10^{-3}$ to 0.1.

In special embodiments of the inventive process, it is also possible to use derivatives or special cases of compounds of the formula I.

Preferably catalysts of the formula II are used, that is to say compounds according to formula I where Q=C and m=1,

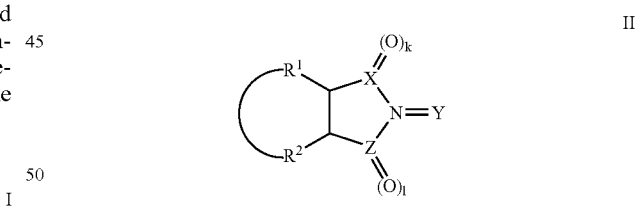

where $R^1$, $R^2$, X, Y, Z, k and l have the meanings defined for compounds of the formula I.

Very particular preference is given to catalysts of the formula III

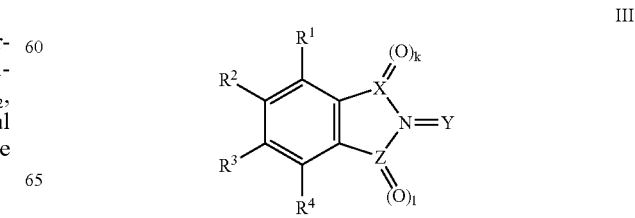

where $R^1$, $R^2$, $R^3$, $R^4$=H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$, where $R^1$, $R^2$, $R^3$ and $R^4$ can be identical or different radicals, X, Z=C, S and/or $CH_2$, Y=0 or OH, k=0, 1 or 2 and l=0, 1 or 2, where k and l must not simultaneously have the value 0.

The inventive oxidation is preferably performed in the liquid phase at a temperature of 0 to 300° C., preferably at a temperature of 50 to 200° C. Not only a solvent or solvent mixture, but also the compound which itself is to be oxidized can be used as solvent here.

The compounds to be oxidized generally belong to the group of hydrocarbons. Using the inventive process, a multiplicity of unsaturated organic compounds such as unbranched and branched alkenes, dienes and trienes having a carbon number from 3 to 25 and substituted and unsubstituted cycloalkenes, substituted and unsubstituted cyclic dienes and also substituted and unsubstituted trienes having a ring number of 5 to 25 can be oxidized and subsequently hydrogenated, the corresponding alcohols, ketones, aldehydes and/or carboxylic acids being produced in high selectivity. Of course, the compounds to be oxidized can also contain heteroatoms, such as nitrogen, oxygen or sulfur, in the chain or the ring. In particular the process according to the present invention can be used for oxidizing cyclic hydrocarbons such as cyclohexene, cyclohexadiene, substituted unsaturated cyclic $C_6$ compounds, cycloheptene, cycloheptadiene, substituted unsaturated cyclic $C_7$ compounds, cyclooctene, cyclooctadiene, substituted unsaturated cyclic $C_8$ compounds, cyclononene, cyclononadiene, substituted unsaturated cyclic $C_9$ compounds, cyclodecene, cyclodecadiene, substituted unsaturated cyclic $C_{10}$ compounds, cycloundecene, cycloundecadiene, substituted unsaturated cyclic $C_{11}$ compounds, cyclododecene, cyclododecadiene, cyclododecatriene, substituted unsaturated cyclic $C_{12}$ compounds, cyclopentadecene, cyclopentadecadiene, cyclopentadecatriene, substituted unsaturated cyclic $C_{15}$ compounds, trivinylcyclohexane or trivinylcyclohexene.

The inventive allylic oxidation of one of the abovementioned compounds produces a a mixture of a plurality of compounds. Thus analysis of the oxidation products by means of gas chromatography shows a multiplicity of compounds. The number of the compounds and the compounds themselves are, however, not critical to the invention, since the oxidation products are only intermediates in the preparation of the alcohols, ketones, aldehydes or carboxylic acids. The oxidation products are fed to a hydrogenation. The hydrogenation product, surprisingly, with high selectivity, has fewer compounds than before the hydrogenation.

The reaction mixture can also comprise a free-radical initiator which is either a free-radical itself or decomposes to form free-radicals, such as a peroxy compound or an azo compound. Examples of such compounds are cumene hydroperoxide, cyclohexylbenzene hydroperoxide, cyclododecylbenzene hydroperoxide, ethylbenzene hydroperoxide, 1,4-di(2-neodecanoylperoxyisopropyl)benzene, acetylcyclohexanesulfonyl peroxide, cumyl peroxyneodecanoate, dicyclohexyl peroxydicarbonate, di(4-tert-butylcyclohexyl) peroxydicarbonate, di(2-ethylhexyl) peroxydicarbonate, dimyristyl peroxydicarbonate, dicetyl peroxydicarbonate, tert-butyl peroxyneodecanoate, tert-amyl peroxyneodecanoate, tert-amyl peroxypivalate, tert-butyl peroxypivalate, diisononanoyl peroxide, didecanoyl peroxide, tert-butyl peroxy-2-ethylhexanoate, tert-butyl peroxyisononanoate, 2,2'-di-tert-butylperoxybutane, ditert-butyl peroxybenzoate, di-tert-butyl peroxide, tertbutyl hydroperoxide, 3,4-dimethyl-3,4-diphenylhexane, dibenzoyl peroxide, 1,4-di-tert-butylperoxycyclohexane, tert-butyl peroxyethylhexylcarbonate, 1,1-di-tert-butylperoxycyclohexane, 2,2'-azobis(2,4-dimethylvaleronitrile), 2,2'-azobis (4-methoxy-2,4-dimethylvaleronitrile), 2,2'-azobis(2-methylpropionitrile), 1,1'-azobis(cyclohexanecarbonitrile) or cyclohexylhydroperoxide. Obviously, peroxides and in particular azo compounds formed as intermediates can also be used as free-radical initiators.

Preference is given to a free-radical initiator which contains an oxygen atom bound to a secondary or tertiary carbon atom. Particular preference is given to a free-radical initiator which is derived from the end product and contains at least one oxygen atom bound to a or tertiary carbon atom. Very particular preference is given to azo initiators. The free-radical initiator is either added separately or as mentioned above generated as an intermediate during the reaction. The free-radical initiator, if the reaction vessel cannot be absolutely cleaned, can also still be present in the reaction vessel in small amounts from preceding reactions.

The concentration of the free-radical initiator in the inventive process is frequently lower at the start of the reaction than the concentration of the catalyst. It must be noted, however, that in the course of the reaction the free-radical initiator can be formed as an intermediate, so that the concentration of free-radical initiating compounds can increase in the course of the reaction.

The oxidation products formed can in principle be isolated as such; according to the invention direct subsequent hydrogenation is the rule. This is carried out either in the same reaction vessel or it takes place as a second stage in a separate reaction container.

The inventive process can be carried out not only batchwise but also continuously.

The inventive process can be carried out using an oxygen-containing gas as oxidizing agent. The proportion of oxygen in the gas can be from 5 to 100% by volume. Preferably, atmospheric oxygen or pure oxygen is used as oxidizing agent. In every case intimate mixture of the liquid and gaseous phases must be ensured. This can be achieved, for example, in stirred tanks by an appropriate stirrer speed or by internals, and in tubular reactors with packing elements and also with bubble columns.

The inventive process can be carried out not only at atmospheric pressure but also at elevated pressure up to 100 bar. Preference is given to a pressure of 1 bar to 50 bar, particular preference is given to a pressure of 1 bar to 20 bar.

The hydrogenation is carried out using hydrogen, for example in appropriate reaction vessels at elevated pressure up to 100 bar, preferably up to 50 bar, very particularly preferably up to 20 bar, and in a special embodiment up to 10 bar, using suitable catalysts, for example the Ru/C catalyst (Engelhard Corp., 101 Wood Av., Iselin, N.J. 08830-0770). It can be advantageous for the hydrogenation to separate off the oxidation catalyst from the oxidation products before the hydrogenation. This can be separated off in various ways, for example by the use of a membrane or by addition of a solvent in which the catalyst is insoluble and subsequent phase separation. Solvents of this type are, for example, chlorinated hydrocarbons, for example carbon tetrachloride. Obviously, not only said hydrogenation catalyst, but also a multiplicity of commercially conventional catalysts offered for this purpose can be used. Preference is given to the Ru/C catalyst from Engelhard. From $10^{-5}$ to $10^2$ mol %, particularly preferably from $10^{-3}$ to 20 mol %, and very particularly preferably from $10^{-2}$ to 10 mol %, are used thereof, based on the substrate. The hydrogenation is carried out at a temperature of 0 to 500° C., preferably from 20 to 300° C., very particularly preferably from 40 to 200° C.

The examples below are intended to illustrate the inventive process in more detail, without restricting the invention to these processes.

Abbreviations

PhCN=benzonitrile

NHPI=N-hydroxyphthalimide

V-65=2,2'-azobis(2,4-dimethylvaleronitrile)

V-70=2,2'-azobis(4-methoxy-2,4-dimethylvaleronitrile)

DCP=dibenzoyl peroxide

CDT=cyclododecatriene

EXAMPLE 1

According to the Invention 2 mmol of CDT, 5 ml of acetone, 8 mol % of NHPI, 1 mol % of V-70 are stirred for 5 hours at a temperature of 50° C. in a round-bottomed flask having an attached reflux condenser. In the course of this oxygen is passed through the mixture at a pressure of 1 bar. After hydrogenation has been carried out using 5 mol % of the catalyst Ru/C in a laboratory autoclave at 10 bar pressure and a temperature of 100° C., cyclododecanone and cyclododecanol are obtained in a ratio of about 1:1 at a conversion rate of 15% CDT in a selectivity of 98%.

EXAMPLE 2

According to the Invention 2 mmol of CDT, 5 ml of PhCN, 4 mol % of NHPI, 1 mol % of V-65 are stirred for 24 hours at a temperature of 70° C. in a round-bottomed flask having an attached reflux condenser. In the course of this oxygen is passed through the mixture at a pressure of 1 bar. After hydrogenation has been carried out using 5 mol % of catalyst Ru/C at 100° C. in a laboratory autoclave at 15 bar pressure, cyclododecanone and cyclododecanol are obtained in a ratio of about 1:1 at a conversion rate of 55% CDT in a selectivity of 81%.

EXAMPLE 3

According to the Invention, without Separate Solvent 2 mmol of CDT, 4 ml of CDT (as solvent), 2 mol % of NHPI, 1 mol % of DBP are stirred for 6 hours at a of 50° C. in a round-bottomed flask having an attached reflux condenser. In the course of this oxygen is passed through the mixture at a pressure of 1 bar. After hydrogenation has been carried out using 5 mol % of catalyst Ru/C at 100° C. in a laboratory autoclave at 8 bar pressure, cyclododecanone and cyclododecanol are obtained in a ratio of about 1:1 at a conversion rate of 22% CDT (in total, that is to say including CDT as solvent) in a selectivity of 79%.

EXAMPLE 4

Not According to the Invention, without NHPI 2 mmol of CDT, 5 ml of acetone and 1 mol % of V-70 are stirred for 5 hours at a temperature of 50° C. in a round-bottomed flask having an attached reflux condenser. In the course of this oxygen is passed through the mixture at a pressure of 1 bar. After hydrogenation has been carried out using 5 mol % catalyst Ru/C at 100° C. in a laboratory autoclave at 8 bar pressure, a cyclododecanone/cyclododecanol 1:1 mixture is obtained at a conversion rate of 4% CDT in a selectivity of 12%.

EXAMPLE 5

Not According to the Invention, with Cobalt Catalyst 2 mmol of CDT, 5 ml of PhCN, 4 mol % of NHPI and 4 mol % of Co(II) acetate are stirred for 24 hours at a temperature of 70° C. in a round-bottomed flask having an attached reflux condenser. In the course of this oxygen is passed through the mixture at a pressure of 1 bar. After hydrogenation has been carried out using 5 mol % of catalyst Ru/C at 100° C. in a laboratory autoclave at 8 bar pressure, a cyclododecanone/cyclododecanol mixture is obtained at a conversion rate of 67% CDT in a selectivity of 6%.

The invention claimed is:

1. A process for preparing saturated alcohols, ketones, aldehydes and carboxylic acids, comprising:
    oxidizing an unsaturated hydrocarbon with an oxygen-containing gas in the presence of a catalyst and a free-radical initiator, and
    reducing the oxidation products by a subsequent hydrogenation to form saturated alcohols, ketones, aldehydes and/or ketones;
    wherein said catalyst is a compound of formula I:

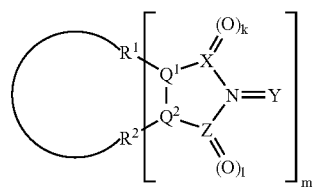

where
$R^1$ and $R^2$ are, independently, H, an aliphatic alkoxy radical, an aromatic alkoxy radical, a carboxyl radical, an alkoxycarbonyl radical or a hydrocarbon radical, each of which has 1 to 20 carbon atoms, $SO_3H$, $NH_2$, OH, F, Cl, Br, I and/or $NO_2$,
wherein $R^1$ and $R^2$ are identical or different radicals, or $R^1$ and $R^2$ can be linked to one another via a covalent bond,
$Q_1$ and $Q_2$ are, independently, C, CH or N, identical or different,
X and Z are, independently, C, S or $CH_2$,
Y is O or OH,
k=0, 1 or 2,
l=0, 1 or 2 and
m=1 to 100.

2. The process of claim 1, wherein the catalyst is a compound of the formula:

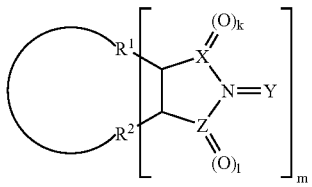

where $R^1$, $R^2$=H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$, where $R^1$ and $R^2$ are identical or different radicals, or $R^1$ and $R^2$ can be linked to one another via a covalent bond,
X and Z are, independently, C, S or $CH_2$,
Y is O or OH,
k=0, 1 or 2,
l=0, 1 or 2 and
m=1 to 3.

3. The process of claim 1, wherein the catalyst is a compound of the formula:

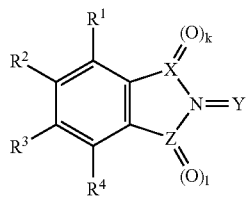

where $R^1$, $R^2$, $R^3$ and $R^4$=H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$, where $R^1$, $R^2$, $R^3$ and $R^4$ can be identical or different radicals,
X and Z are, independently, C, S or $CH_2$,
Y is O or OH,
k=0, 1 or 2 and
l=0, 1 or 2.

4. The process of claim 1, wherein said catalyst is a hydantoin derivative of the formula:

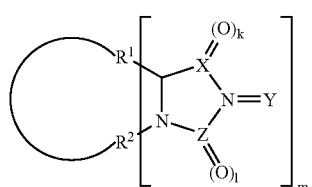

where $R^1$ and $R^2$ are, independently, H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$,
where $R^1$ and $R^2$ are identical or different radicals, or $R^1$ and $R^2$ can be linked to one another via a covalent bond,
X and Z are, independently, C, S or $CH_2$,
Y is O or OH,
k=0, 1 or 2,
l=0, 1 or 2 and
m=1 to 3.

5. The process of claim 1, wherein the unsaturated hydrocarbon is an unbranched or branched alkene, alkyne, diene or triene having a carbon number from 3 to 25.

6. The process of claim 1, wherein the unsaturated hydrocarbon is a cyclic alkene, diene or triene having 5 to 25 ring atoms.

7. The process of claim 6, wherein the cyclic hydrocarbon to be oxidized is at least one compound selected from the group consisting of cyclohexene, cyclohexadiene, substituted unsaturated cyclic $C_6$ compounds, cycloheptene, cycloheptadiene, substituted unsaturated cyclic $C_7$ compounds, cyclooctene, cyclooctadiene, substituted unsaturated cyclic $C_8$ compounds, cyclononene, cyclononadiene, substituted unsaturated cyclic $C_9$ compounds, cyclodecene, cyclodecadiene, substituted unsaturated cyclic $C_{10}$ compounds, cycloundecene, cycloundecadiene, substituted unsaturated cyclic $C_{11}$ compounds, cyclododecene, cyclododecadiene, cyclododecatriene, substituted unsaturated cyclic $C_{12}$ compounds, cyclopentadecene, cyclopentadecadiene, cyclopentadecatriene, substituted unsaturated cyclic $C_{15}$ compounds, trivinylcyclohexene and trivinylcyclohexene.

8. The process of claim 1, wherein the free-radical initiator is a peroxy compound or azo compound.

9. The process of claim 1, wherein the catalytic oxidation is carried out at a temperature of 0 to 500° C.

10. The process of claim 1, wherein the oxidizing agent is a gas which comprises 5 to 100% by volume of oxygen.

11. The process of claim 1, wherein the catalytic oxidation is carried out at a pressure of 1 to 100 bar.

12. The process of claim 1, wherein $R^1$ and $R^2$ are, independently, an aliphatic alkoxy radical, an aromatic alkoxy radical, a carboxyl radical, an alkoxycarbonyl radical or a hydrocarbon radical, each of which has 1 to 20 carbon atoms.

13. The process of claim 1, wherein $R^1$ and $R^2$ are, independently, H, $SO_3H$, $NH_2$, OH, F, Cl, Br, I and/or $NO_2$.

14. The process of claim 1, wherein $R^1$ and $R^2$ are linked to one another via a covalent bond.

15. The process of claim 1, wherein $Q_1$ and $Q$, are independently, C or CH.

16. The process of claim 1, wherein at least one of $Q_1$ and Q is N.

17. The process of claim 1, wherein X and Z are, independently, C or $CH_2$.

18. The process of claim 1, wherein at least one of X and Z is S.

19. The process of claim 1, wherein Y is O.

20. The process of claim 1, wherein Y is OH.

* * * * *